United States Patent
Kizuka

(10) Patent No.: US 11,027,094 B2
(45) Date of Patent: Jun. 8, 2021

(54) TUBULAR BODY AND CATHETER HAVING TUBULAR BODY

(71) Applicant: ASAHI INTECC CO., LTD., Seto (JP)

(72) Inventor: Takeshi Kizuka, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 239 days.

(21) Appl. No.: 16/424,928

(22) Filed: May 29, 2019

(65) Prior Publication Data

US 2019/0275288 A1 Sep. 12, 2019

Related U.S. Application Data

(63) Continuation of application No. PCT/JP2017/014407, filed on Apr. 6, 2017.

(51) Int. Cl.
*A61M 25/00* (2006.01)

(52) U.S. Cl.
CPC .......... *A61M 25/005* (2013.01); *A61M 25/00* (2013.01); *A61M 25/0068* (2013.01); *A61M 25/0097* (2013.01)

(58) Field of Classification Search
CPC ................................................ A61M 25/0024
See application file for complete search history.

(56) References Cited

U.S. PATENT DOCUMENTS

| 7,002,072 | B2 * | 2/2006 | Tonucci | H01B 3/105 |
| | | | | 174/36 |
| 2003/0093060 | A1 * | 5/2003 | Kempf | A61M 25/0043 |
| | | | | 604/527 |
| 2006/0265037 | A1 * | 11/2006 | Kuzma | A61N 1/0551 |
| | | | | 607/116 |
| 2011/0106056 | A1 | 5/2011 | Hatano et al. | |
| 2016/0220787 | A1 * | 8/2016 | Plassman | A61M 25/0054 |

FOREIGN PATENT DOCUMENTS

| JP | 2001-218851 A | | 8/2001 | |
| JP | 2007-75531 A | | 3/2007 | |
| JP | 2007075531 A | * | 3/2007 | ............ A61M 25/09 |
| JP | 2013-165926 A | | 8/2013 | |
| JP | 2013165926 A | * | 8/2013 | |
| JP | 2015-65979 A | | 4/2015 | |
| JP | 2015065979 A | * | 4/2015 | |
| JP | 2015-156959 A | | 9/2015 | |

OTHER PUBLICATIONS

Jun. 13, 2017 International Search Report issued in International Patent Application No. PCT/JP2017/014407.

* cited by examiner

*Primary Examiner* — Bhisma Mehta
*Assistant Examiner* — Robert F Allen
(74) *Attorney, Agent, or Firm* — Oliff PLC

(57) ABSTRACT

A catheter having excellent flexibility in order to follow a guidewire, and that is not easily kinked even when the catheter is bent strongly. The catheter includes a catheter shaft having a hollow resin body and a coil body within the hollow resin body. The coil body is formed of a spirally wound wire, which is slidable with respect to the hollow resin body.

6 Claims, 10 Drawing Sheets

TUBULAR BODY AND CATHETER HAVING TUBULAR BODY

CROSS REFERENCE TO RELATED APPLICATION

This is a Continuation of PCT/JP2017/014407 filed Apr. 6, 2017. The disclosure of the prior application is hereby incorporated by reference herein in its entirety.

BACKGROUND

The disclosed embodiments relate to a medical device, and in particular to a tube and a catheter comprising the tube.

Stricture sites or obliteration sites formed in internal lumina such as blood vessels, bile ducts, or pancreatic ducts inhibit the proper flow of blood, bile, pancreatic juice, and the like in internal lumina. To ameliorate such flow, methods for treating stricture sites or obliteration sites using catheters have been widely performed.

In general, internal lumina such as blood vessels, bile ducts, and pancreatic ducts taper toward the ends such that they become narrower, and are strongly curved. When a guidewire is inserted into the internal lumen, it will follow the curvature of the internal lumen and thus will be strongly bent. Any catheter that is advanced into the internal lumen along the guidewire must be sufficiently flexible to follow the strongly bent guidewire, and must have sufficient kink resistance to prevent kinking even when strongly bent.

Japanese Unexamined Patent Publication No. 2001-218851 discloses a catheter 1 comprising an inner layer 7, a coil 3 wound around the outer circumference of the inner layer 7, and an outer layer 8 coating the outer circumference of the coil 3 (see, e.g., FIG. 2 of Japanese Unexamined Patent Publication No. 2001-218851).

Furthermore, Japanese Unexamined Patent Publication No. 2013-165926 discloses a catheter 1 comprising an inner layer 13, multiple coils 111 to 114 that are wound around the outer circumference of the inner layer 13 and arranged longitudinally, and an outer layer 12 coating the outer circumference of the coils 111 to 114 (see, e.g., FIG. 2 of Japanese Unexamined Patent Publication No. 2013-165926).

However, in the catheter described in Japanese Unexamined Patent Publication No. 2001-218851, the coil (hereinafter, described as "coil body") is completely fixed over the entire length between the inner layer and the outer layer. Therefore, the catheter is problematic in that when it is bent, a wire(s) forming the coil body is unable to be moved along the bending shape, and thus the catheter has poor flexibility to follow the guidewire.

Furthermore, the catheter described in Japanese Unexamined Patent Publication No. 2013-165926 is also problematic in that since multiple coil bodies are arranged but completely fixed between the inner layer and the outer layer, wires forming the coil bodies are unable to be moved according to the bending shape when the catheter is bent, resulting in poor flexibility to follow the guidewire.

SUMMARY

The disclosed embodiments were devised to address such problems, and an object of the disclosed embodiments is to provide a catheter which is excellent in flexibility to follow a guidewire, and is not easily kinked even when the catheter is strongly bent.

In particular, the disclosed embodiments include a tube (e.g., a catheter shaft) comprising a hollow resin body and a coil body formed of at least one spirally wound wire within the hollow resin body. The wire is slidable with respect to the resin body, which prevents the tube from kinking and improves the flexibility of the tube.

The tube can include gaps between the wire and the resin body in order to further improve the flexibility of the tube. Also, the wire can be fixed at its proximal end to the proximal end section (proximal portion) of the resin body such that the distal end of the resin body has gaps (distal gaps), which further improves the flexibility of the distal end of the tube.

Further, the disclosed embodiments include a tube formed by winding a resin-coated wire comprising a wire and a resin coating covering the wire. Adjacent turns of the resin-coated wire are fixed, and the wire is slidable with respect to the resin coating so as to be able to prevent kinking of the tube and to further improve the flexibility of the tube.

Additionally, the tube can include gaps between the wire and the resin coating in order to further improve the flexibility of the tube. Also, the wire can be fixed at its proximal end to the proximal end section of the resin coating such that the distal end of the resin coating has distal gaps, which further improves the flexibility of the distal end of the tube.

The disclosed embodiments also include a catheter comprising the tube, a distal tip connected to the distal end of the tube, and a connector connected to the proximal end of the tube.

DETAILED DESCRIPTION OF EMBODIMENTS

Hereinafter, embodiments of the present invention are described with reference to the drawings.

First, a catheter of the disclosed embodiments is described with reference to FIG. 1 to FIG. 3.

Figure 1:
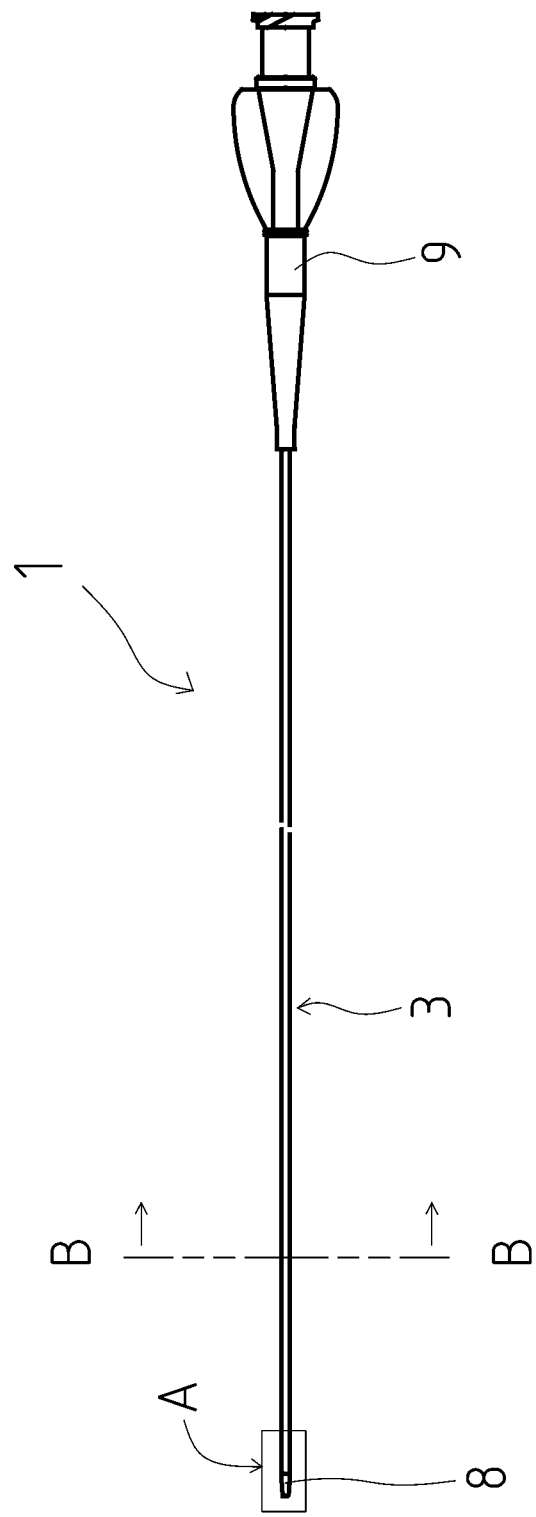
FIG. 1 is a general view of a catheter of the disclosed embodiments.

FIG. 1 is a general view of the catheter. FIG. 2 is an enlarged sectional view of part A of the catheter shown in FIG. 1. FIG. 3 shows a cross section of the catheter shown in FIG. 1 taken along the line B-B.

Figure 2:
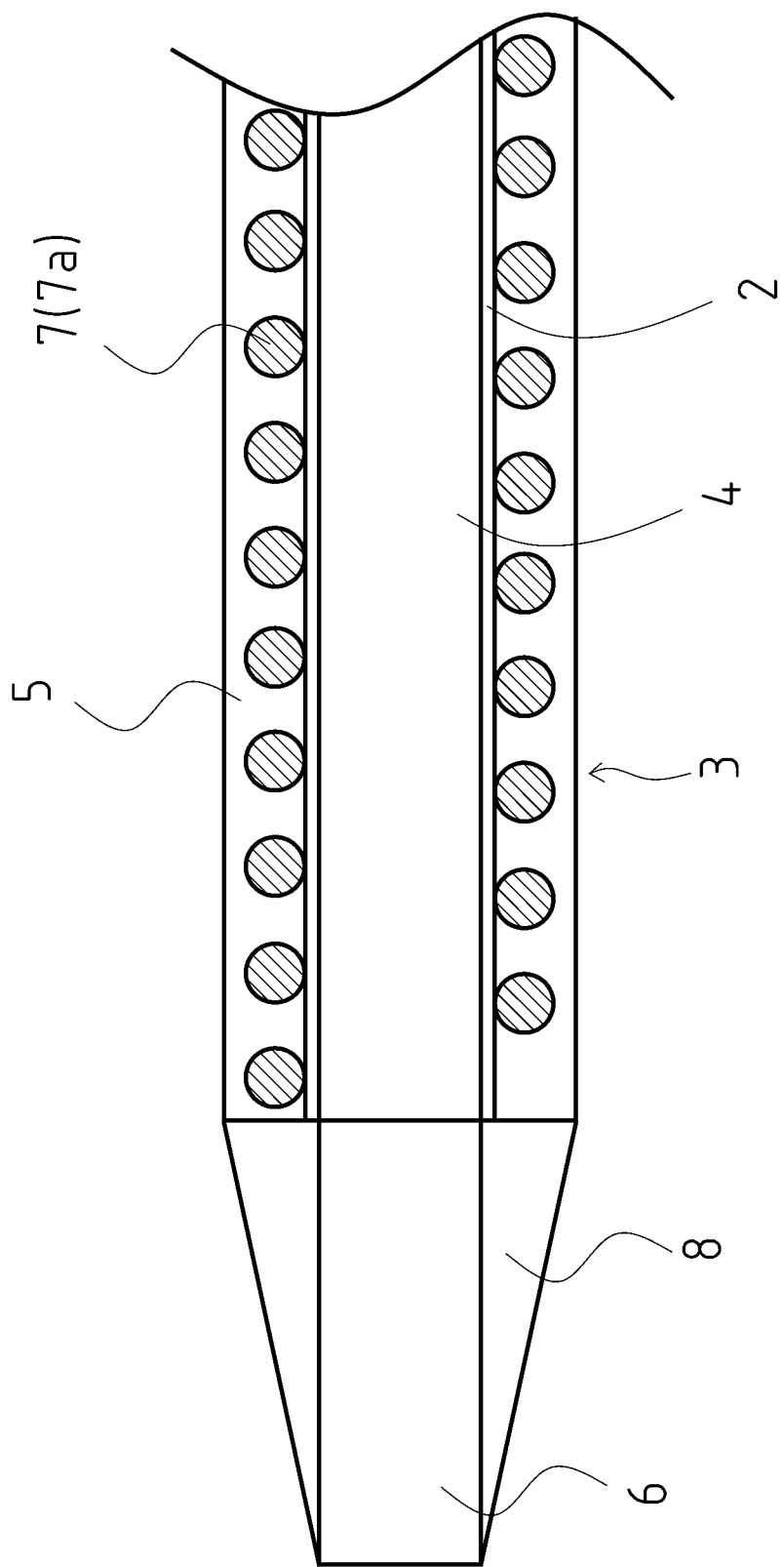
FIG. 2 is an enlarged sectional view of part A of the catheter shown in FIG. 1.
Figure 3:
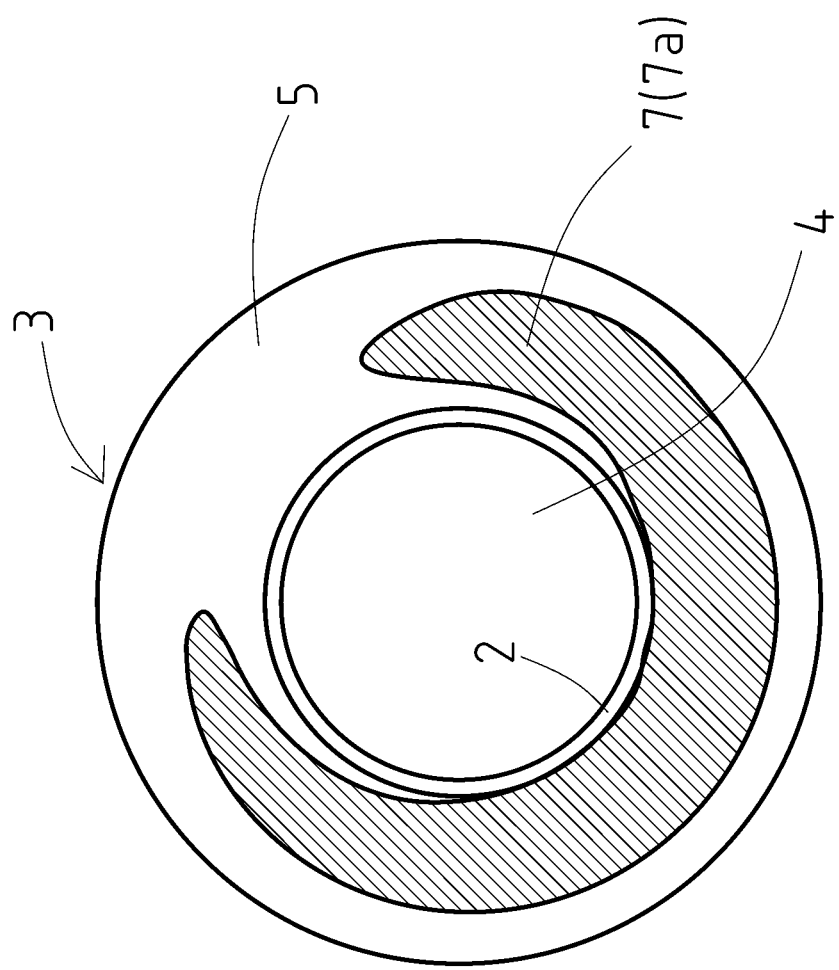
FIG. 3 shows a cross section of the catheter shown in FIG. 1 taken along the line B-B.

In FIG. 1 and FIG. 2, the left side in each figure is a tip side (distal side) to be inserted into a body, and the right side in each figure is the rear side (proximal side) to be operated by a clinician such as a doctor.

In FIG. 1, a catheter 1 comprises a catheter shaft 3 (a tube), a distal tip 8 connected to the distal end of the catheter shaft 3, and a connector 9 connected to the proximal end of the catheter shaft 3.

The catheter shaft 3 forms a hollow cylindrical shape and has, as shown in FIG. 2, sequentially in a radial direction from inside, an inner layer 2, a coil body 7 formed of a wire spirally wound around the outer circumference of the inner layer 2, and an outer layer 5 covering (coating) the outer circumference of the coil body 7. That is, the catheter shaft 3 includes a hollow resin body (comprising the inner layer 2 and the outer layer 5) and a coil body 7 encased (enclosed or embedded) in the hollow resin body.

The inner layer 2 is a hollow tube made of a resin, within which a lumen 4 is formed for insertion of a guidewire or another catheter thereinto. A resin material constituting the inner layer 2 is not particularly limited. For example, the resin material can be PTFE (polytetrafluoroethylene).

As shown in FIG. 2, the coil body 7 is constituted by winding a single wire 7a spirally around the outer circumference of the inner layer 2 such that adjacent wire 7a turns are spaced away from each other. Stainless steel (SUS304) can be used as a material of the wire 7a constituting the coil body 7, but the material is not limited thereto. As the material of the wire 7a constituting the coil body 7, for example, a metal material such as tungsten or a Ni—Ti alloy may be used or a resin material such as reinforced plastic (PEEK) may be used.

Note that, in FIG. 2, the coil body 7 is constituted of a single wire 7a. The coil body 7 may alternatively be constituted of multiple wires. However, the coil body 7 constituted of a single wire can further improve flexibility.

The outer layer 5 is made of a resin and coats the outer circumference of the inner layer 2 and the coil body 7 to form a tube. A resin material for constituting the outer layer 5 is not particularly limited. For example, a polyamide, polyamide elastomer, polyester, polyurethane or the like can be used.

The wire 7a constituting the coil body 7 is arranged to be slidable with respect to the outer layer 5. Specifically, the wire 7a is spirally wound around the outer circumference of the inner layer 2 without being fixed to the inner layer 2 and the outer layer 5, and is therefore spirally slidable (i.e., it can advance distally or proximally by rotating about the longitudinal of the catheter 1 axis via a screwing motion as the catheter 1 bends). That is, the wire 7a is unconstrained with respect to the inner layer 2 and outer layer 5 and is free to rotate about the longitudinal axis of the catheter 1.

Further, the distal tip 8 made of a resin is connected to the distal end of the catheter shaft 3. The distal tip 8 is a hollow tapered member having a lumen 6 communicating with the lumen 4. A resin material constituting the distal tip 8 is not particularly limited. For example, a polyurethane, polyurethane elastomer, or the like can be used.

Further, the distal tip 8 may contain a radiation-impermeable powder in the resin. For example, the distal tip 8 contains, in the resin, radiation-impermeable powder (e.g., tungsten powder) in an amount ranging from about 65 wt % to about 90 wt % with respect to the total resin composition (resin and powder), so that a clinician such as a doctor can precisely determine the position of the catheter 1 upon imaging.

Further, the connector 9 made of a resin is connected to the proximal end of the catheter shaft 3. The connector 9 is a hollow member having a lumen (not shown) communicating with the lumen 4. A resin material constituting the connector 9 is not particularly limited. For example, a polycarbonate or the like can be used.

In the catheter shaft 3 of catheter 1, the wire 7a constituting the coil body 7 is arranged to be slidable with respect to the inner layer 2 and the outer layer 5, which improves the flexibility of the catheter shaft 3 and the catheter 1 and prevents kinking of the catheter shaft 3 and the catheter 1.

Figure 4:
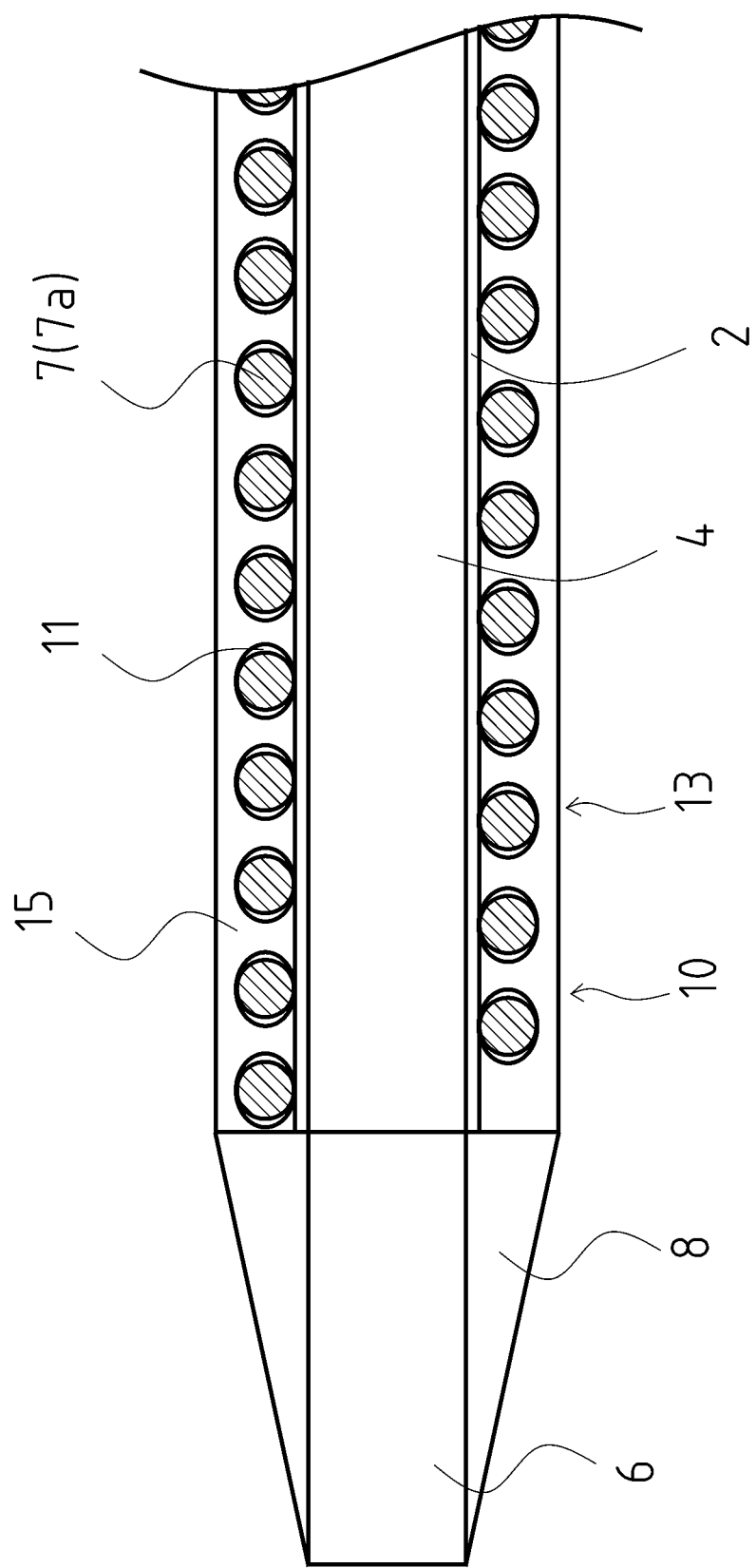
FIG. 4 is a sectional view of a portion of a catheter of the disclosed embodiments.

Next, a catheter of the disclosed embodiments is described with reference to FIG. 4. FIG. 4 is a sectional view of a portion of the catheter.

Members that are the same as the members constituting the catheter 1 are numbered with the same numbers, and descriptions therefor are omitted.

Also in FIG. 4, the left side in the figure is the tip side (distal side) to be inserted into a body, and the right side in the figure is the rear side (proximal side) to be operated by a clinician such as a doctor.

In FIG. 4, a catheter 10 comprises a catheter shaft 13 (a tube), a distal tip 8 connected to the distal end of the catheter shaft 13, and a connector 9 connected to the proximal end of the catheter shaft 13.

The catheter shaft 13 has, as shown in FIG. 4, sequentially in a radial direction from inside, an inner layer 2, a coil body 7 formed of a wire 7a spirally wound around the outer circumference of the inner layer 2, and an outer layer 15 coating the outer circumference of the coil body 7.

The outer layer 15 is made of a resin and coats the outer circumference of the inner layer 2 and the coil body 7 to form a tube. A resin material constituting the outer layer 15 is not particularly limited. For example, a polyamide, polyamide elastomer, polyester, polyurethane or the like can be used.

In the catheter 10, the wire 7a constituting the coil body 7 is arranged in a manner similar to that in catheter 1, such that it is arranged to be slidable with respect to the outer layer 15. Specifically, the wire 7a is spirally wound around the outer circumference of the inner layer 2 without being fixed to the inner layer 2 and the outer layer 5, and is therefore spirally slidable.

The catheter 10 differs from the catheter 1 in that the catheter 10 comprises gap portions 11 formed between the wire 7a constituting the coil body 7 and the outer layer 15; the catheter 1 comprises no such gap portion 11 formed therein.

In the catheter shaft 13 of the catheter 10, the wire 7a constituting the coil body 7 is arranged to be slidable with respect to the inner layer 2 and the outer layer 15 and the gap portions 11 are formed between the wire 7a constituting the coil body 7 and the outer layer 15, so that the flexibility of the catheter shaft 13 and the catheter 10 can be further improved.

Figure 5:
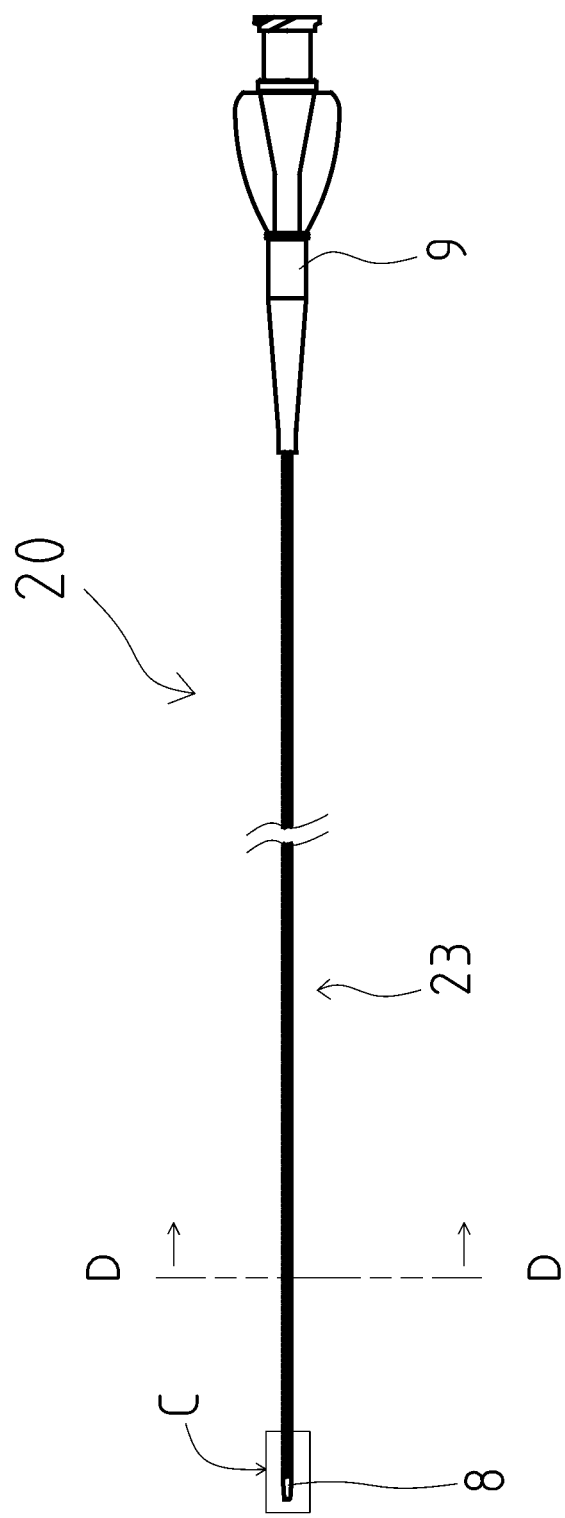
FIG. 5 is a general view of a catheter of the disclosed embodiments.
Figure 6:
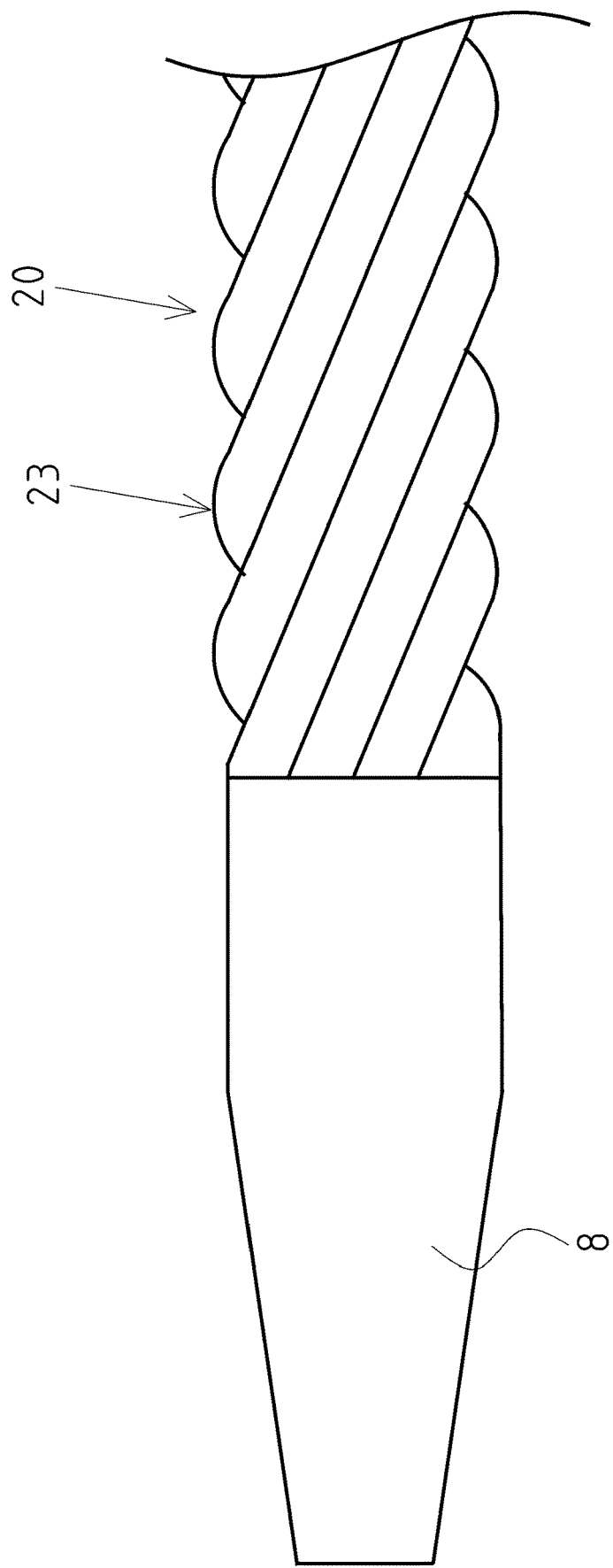
FIG. 6 is an enlarged view of a portion of part C of the catheter shown in FIG. 5.
Figure 7:
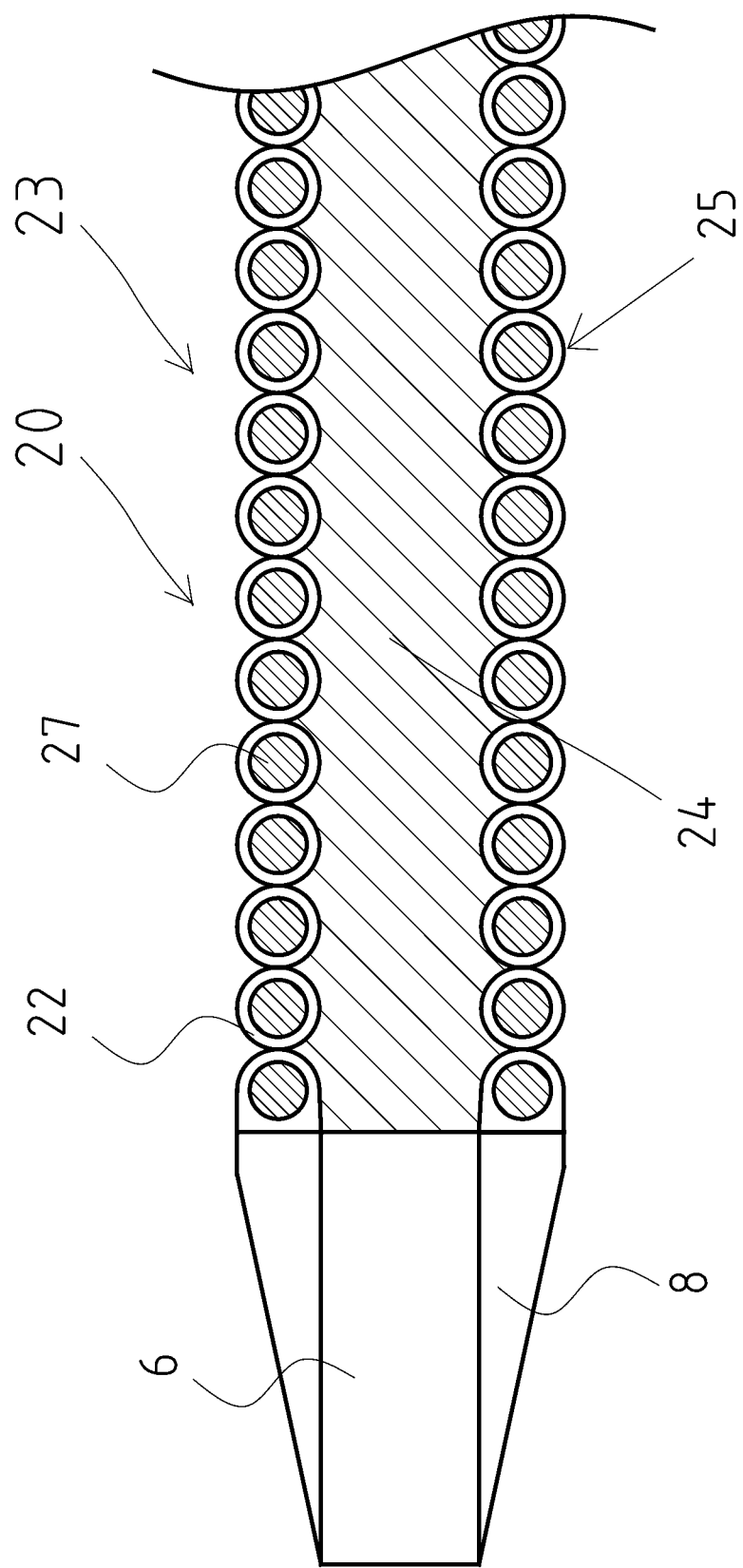
FIG. 7 is an enlarged sectional view of part C of the catheter shown in FIG. 5.
Figure 8:
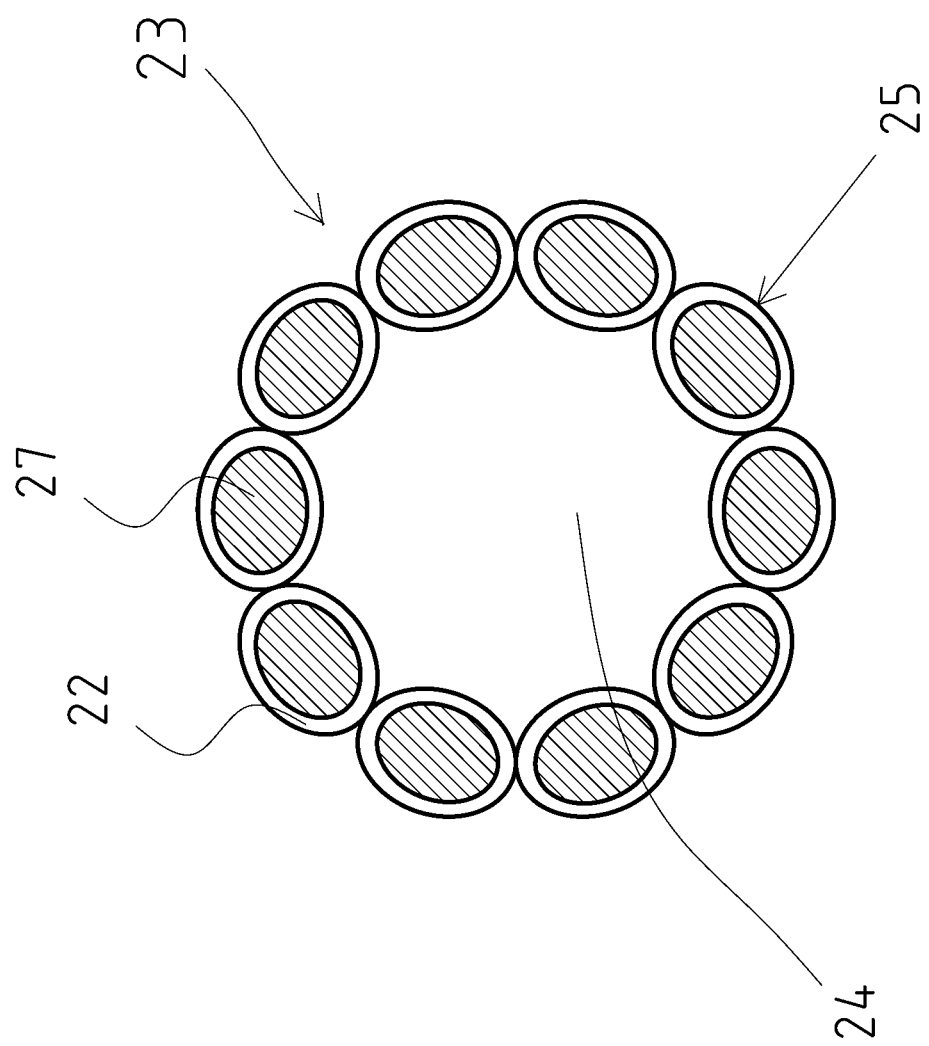
FIG. 8 shows a cross section of the catheter shown in FIG. 5 taken along the line D-D.

Next, a catheter of the disclosed embodiments is described with reference to FIG. 5 to FIG. 8. FIG. 5 is a general view of the catheter. FIG. 6 is an enlarged view of a portion of part C of the catheter shown in FIG. 5. FIG. 7 is an enlarged sectional view of part C of the catheter shown in FIG. 5. FIG. 8 shows a cross section of the catheter shown in FIG. 5 taken along the line D-D.

Members that are the same as the members constituting the catheter 1 are numbered with the same numbers and descriptions therefor are omitted.

Also in FIG. 5 to FIG. 7, the left side in each figure is the tip side (distal side) to be inserted into a body and the left side in each figure is the rear side (proximal side) to be operated by a clinician such as a doctor.

In FIG. 5, a catheter 20 comprises a catheter shaft 23 (a tube), a distal tip 8 connected to the distal end of the catheter shaft 23, and a connector 9 connected to the proximal end of the catheter shaft 23.

The catheter shaft 23 is formed as shown in FIG. 6 to FIG. 8, wherein multiple resin-coated wires 25 (as shown, ten wires), each comprising a wire 27 and a resin film 22 (resin coating) coating the outer circumference of the wire 27, are spirally wound to form a hollow coil body. Here, the adjacent turns of the resin-coated wires 25 are characterized in that contact portions between the resin films 22 of the resin-coated wires 25 are each spirally welded (welded along the length of the resin-coated wires 25 at the contact portions). The catheter shaft 23 constitutes a hollow tube as a whole. Moreover, the catheter shaft 23 forms a lumen 24 with an irregular surface for insertion of a guidewire or another catheter thereinto. The irregular surface includes protrusions corresponding to the shape of the inner surface of the coil formed by spirally winding the resin-coated wires 25, and thus the surface is not a smooth surface.

The wires 27 of catheter 20 are slidable with respect to the resin films 22. Specifically, the wires 27 are spirally wound together with the resin films 22 without being fixed to the resin films 22, and thus the wires 27 are spirally slidable.

A resin material constituting the resin films 22 is not particularly limited. For example, a polyamide, polyamide elastomer, polyester, polyurethane, PTFE (polytetrafluoroethylene) or the like can be used.

In FIG. 5 to FIG. 8, the catheter shaft 23 is constituted of multiple resin-coated wires 25 but may also be constituted of a single resin-coated wire 25. The catheter shaft 23 constituted of a single resin-coated wire can further improve flexibility.

As described above, the catheter shaft 23 can be constituted of ten resin-coated wires 25. However, the number of the resin-coated wires 25 is not limited to ten and may be any number. However, the catheter shaft 23 constituted of a smaller number of resin-coated wires 25 is preferable in view of flexibility.

Further, the distal tip 8 made of a resin is connected to the distal end of the catheter shaft 23. The distal tip 8 is a hollow tapered member having a lumen 6 communicating with a lumen 24.

Moreover, the connector 9 made of a resin is connected to the proximal end of the catheter shaft 23. The connector 9 is a hollow member having a lumen (not shown) communicating with the lumen 24.

In the catheter shaft 23 of the catheter 20, the wires 27 are arranged to be slidable with respect to the resin films 22, so that the flexibility of the catheter shaft 23 and that of the catheter 20 can be improved and kinking of the catheter shaft 23 and the catheter 20 can be prevented.

Figure 9:
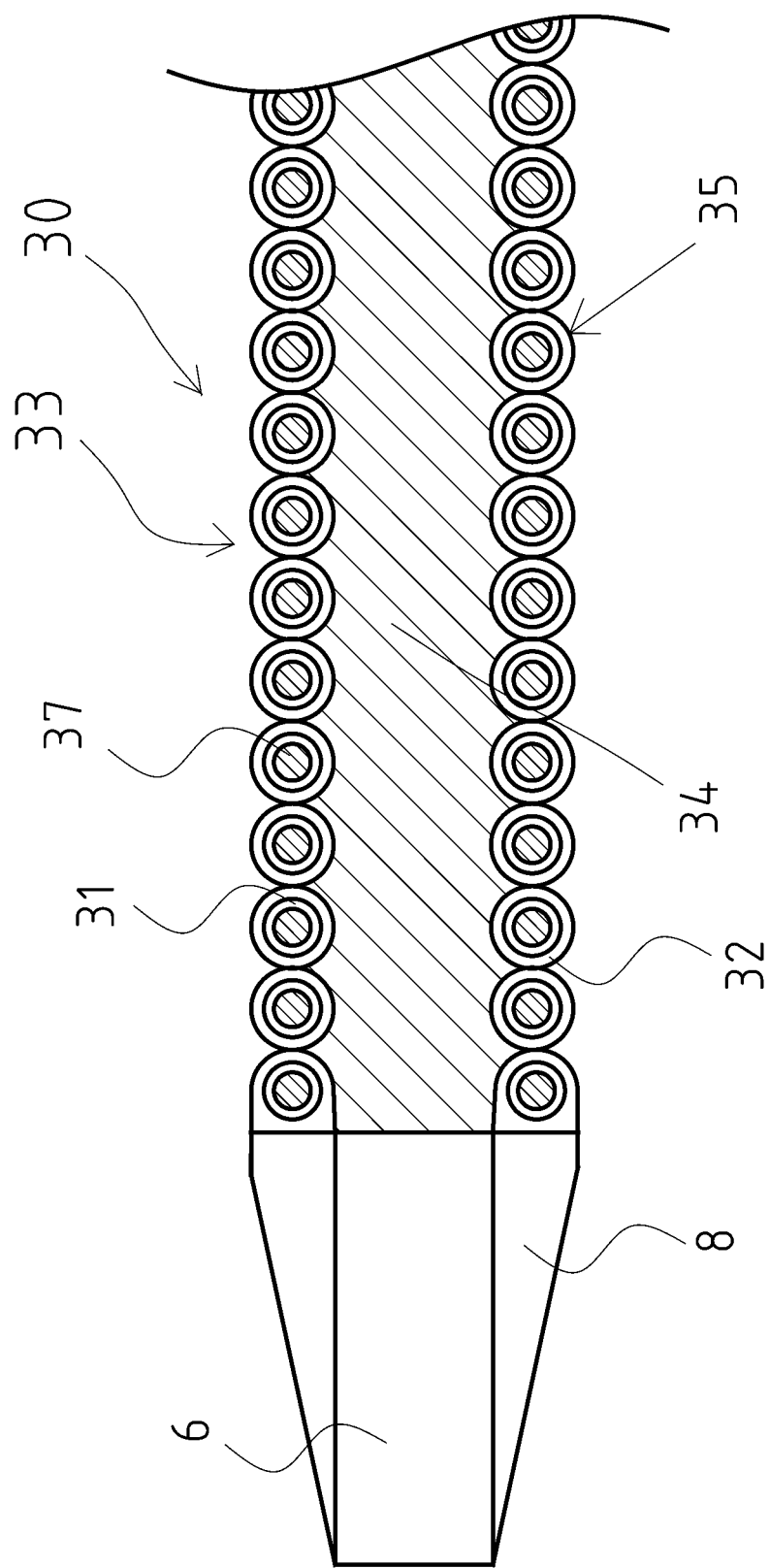
FIG. 9 is a sectional view of a portion of a catheter of the disclosed embodiments.

A catheter of the disclosed embodiments is described with reference to FIG. 9. FIG. 9 is a sectional view of a portion of the catheter.

Members that are the same as the members constituting the catheter 20 are numbered with the same numbers and descriptions therefor are omitted.

Also in FIG. 9, the left side in the figure is a tip side (distal side) to be inserted into a body, and the right side in the figure is the rear side (proximal side) to be operated by a clinician such as a doctor.

In FIG. 9, a catheter 30 comprises a catheter shaft 33 (a tube), a distal tip 8 connected to the distal end of the catheter shaft 33, and a connector 9 connected to the proximal end of the catheter shaft 33.

The catheter shaft 33 is formed as shown in FIG. 9, wherein multiple resin-coated wires 35 (e.g., ten wires), each comprising a wire 37 and a resin film 32 coating the outer circumference of the wire 37, are spirally wound to form a hollow coil body. Here, the adjacent turns of the resin-coated wires 35 are characterized in that contact portions between the resin films 32 of the resin-coated wires 35 are each spirally welded. The catheter shaft 33 constitutes a hollow tube as a whole. Moreover, the catheter shaft 33 forms a lumen 34 with an irregular surface for insertion of a guidewire or another catheter thereinto.

The wires 37 of the catheter 30 are slidable with respect to the resin films 32. Specifically, the wires 37 are spirally wound together with the resin films 32 without being fixed to the resin films 32, and are therefore spirally slidable.

A resin material constituting the resin films 32 is not particularly limited. For example, a polyamide, polyamide elastomer, polyester, polyurethane, PTFE (polytetrafluoroethylene) or the like can be used.

In FIG. 9, the catheter shaft 33 is constituted of multiple resin-coated wires 35 but may also be constituted of a single resin-coated wire 35. The catheter shaft 33 constituted of a single resin-coated wire is preferable in view of flexibility.

As described above, the catheter shaft 33 can be constituted of ten resin-coated wires 35. However, the number of the wires 35 is not limited to ten and may be any number of wires. However, the catheter shaft 33 constituted of a smaller number of resin-coated wires is preferable in view of flexibility.

Moreover, the distal tip 8 made of a resin is connected to the distal end of the catheter shaft 33. The distal tip 8 is a hollow tapered member having a lumen 6 communicating with a lumen 34.

The connector 9 made of a resin is connected to the proximal end of the catheter shaft 33. The connector 9 is a hollow member having a lumen (not shown) communicating with the lumen 34.

The catheter 30 differs from the catheter 20 in that the catheter 30 comprises gap portions 31 formed between the wires 37 and the resin films 32; the catheter 20 comprises no such gap portion formed therein.

Therefore, in the catheter shaft 33 of the catheter 30, the wires 37 are arranged to be slidable with respect to the resin films 32, and the gap portions 31 are formed between the wires 37 and the resin films 32, so that flexibility of the catheter shaft 33 and the catheter 30 can further be improved.

Figure 10:
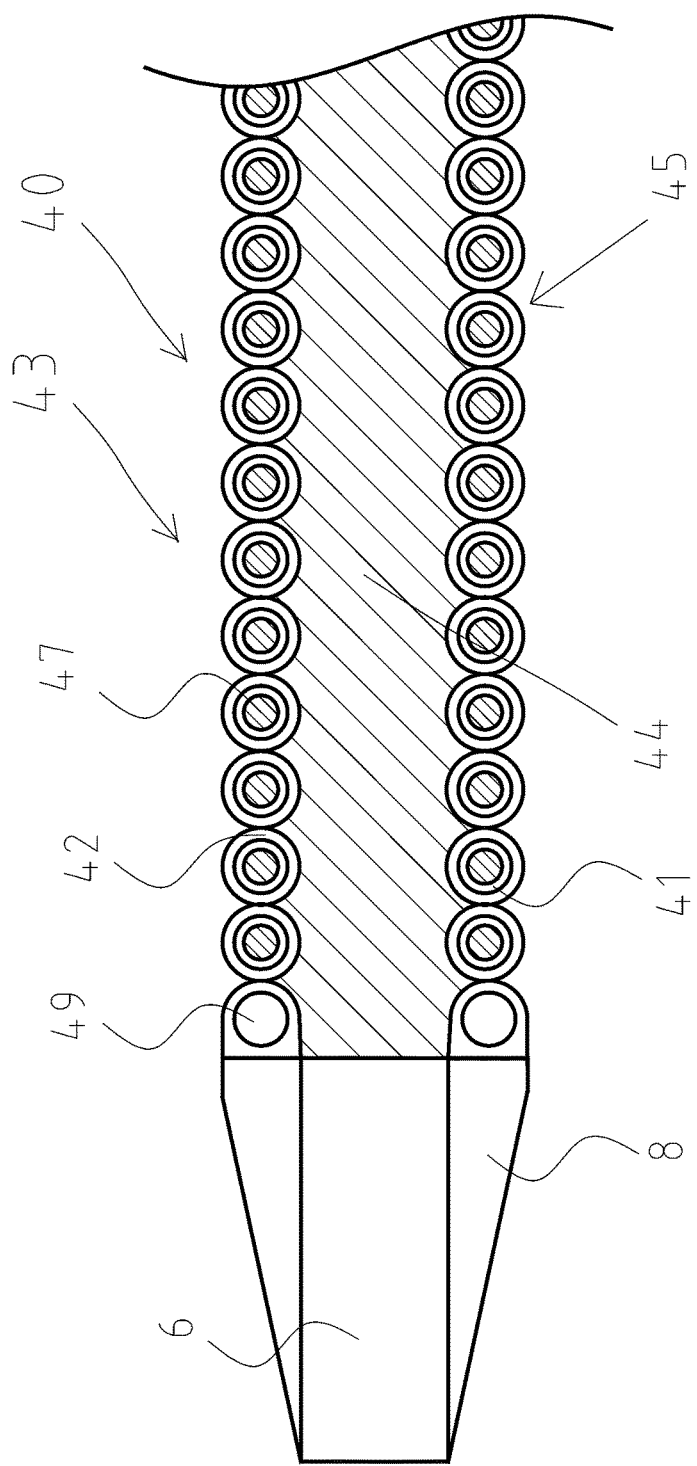
FIG. 10 is a sectional view of a portion of a catheter of the disclosed embodiments.

Finally, a catheter of the disclosed embodiments is described with reference to FIG. 10. FIG. 10 is a sectional view of a portion of the catheter.

Members that are the same as the members constituting the catheter 20 are numbered with the same numbers and descriptions therefor are omitted.

Also in FIG. 10, the left side in the figure is the tip side (distal side) to be inserted into a body, and the right side in the figure is the rear side (proximal side) to be operated by a clinician such as a doctor.

In FIG. 10, a catheter 40 comprises a catheter shaft 43 (a tube), a distal tip 8 connected to the distal end of the catheter shaft 43, and a connector 9 connected to the proximal end of the catheter shaft 43.

The catheter shaft 43 is formed as shown in FIG. 10, wherein multiple resin-coated wires 45 (e.g., ten wires), each comprising a wire 47 and a resin film 42 coating the outer circumference of the wire 47, are spirally wound to form a hollow coil body. Here, the adjacent turns of the resin-coated wires 45 are characterized in that contact portions between the resin films 42 of the resin-coated wires 45 are each spirally welded. The catheter shaft 43 constitutes a hollow tube as a whole. The catheter shaft 43 forms a lumen 44 with an irregular surface for insertion of a guidewire or another catheter thereinto.

The wires 47 of the catheter 40 are slidable with respect to the resin films 42 at portions other than the proximal ends. Specifically, the wires 47 are spirally wound together with the resin films 42 while the portions other than the proximal ends of the wires 47 are not fixed to the resin films 42, and thus the wires 47 are spirally slidable.

Furthermore, the catheter 40 comprises gap portions 41 between the wires 47 and the resin films 32. Therefore, the flexibility of the catheter shaft 43 and the catheter 40 can further be improved.

A resin material constituting the resin films 42 is not particularly limited. For example, a polyamide, polyamide elastomer, polyester, polyurethane, PTFE (polytetrafluoroethylene) or the like can be used.

Note that in the catheter 40, the catheter shaft 43 is constituted of multiple resin-coated wires 45 but may also be constituted of a single resin-coated wire 45. The catheter shaft 43 constituted of a single resin-coated wire is preferable in view of flexibility.

Further, as described above, the catheter shaft 43 can be constituted of ten resin-coated wires 45. However, the number of the wires 45 is not limited to ten and may be any number of wires. However, the catheter shaft 43 constituted of a smaller number of resin-coated wires is preferable in view of flexibility.

Moreover, the distal tip 8 made of a resin is connected to the distal end of the catheter shaft 43. The distal tip 8 is a hollow tapered member having a lumen 6 communicating with a lumen 44.

Moreover, the connector 9 made of a resin is connected to the proximal end of the catheter shaft 43. The connector 9 is a hollow member having a lumen (not shown) communicating with the lumen 44.

The catheter 40 differs from the catheter 30 in that the wires 47 in the catheter 40 are fixed at their proximal ends to the resin films 42, and gap portions 49 (distal gap portions) are formed in the distal portions of the resin films 42 where no wires 47 are present; the catheter 30 comprises no such distal gap portion formed therein.

Therefore, in the catheter shaft 43 of the catheter 40, the wires 47 are arranged to be slidable with respect to the resin films 42, the gap portions 41 are formed between the wires 47 and the resin films 42, and gap portions 49 are formed in the distal portions of the resin films 42 where no wires 47 are present, so that the flexibility of the catheter shaft 43 and the catheter 40, and particularly the flexibility at the distal portions, can be further improved.

What is claimed is:

1. A tube comprising:
    a hollow coil body formed of a spirally wound resin-coated wire, the resin-coated wire comprising a wire and a resin coating covering the wire, wherein:
    adjacent turns of the resin-coated wire are fixed at contact portions between adjacent portions of the resin coating, and
    the wire is slidable with respect to the resin coating.

2. The tube according to claim 1, further comprising a gap between the wire and the resin coating along a length of the wire.

3. The tube according to claim 2, wherein the gap extends along the entire length of the wire.

4. The tube according to claim 1, wherein a proximal end of the wire is fixed to the resin coating.

5. The tube according to claim 2, further comprising a distal gap portion distal to a distal end of the wire.

6. A catheter comprising:
    the tube according to claim 1;
    a distal tip connected to a distal end of the tube; and
    a connector connected to a proximal end of the tube.

* * * * *